United States Patent [19]

Rasmussen

[11] Patent Number: 5,696,115
[45] Date of Patent: Dec. 9, 1997

US005696115A

[54] METHOD FOR TREATING NICOTINE WITHDRAWAL

[75] Inventor: Kurt Rasmussen, Fishers, Ind.

[73] Assignee: Eli Lilly and Company, Indianapolis, Ind.

[21] Appl. No.: 422,202

[22] Filed: Apr. 21, 1995

[51] Int. Cl.[6] .................................. A61K 31/55
[52] U.S. Cl. ............................. 514/220; 514/813
[58] Field of Search .......................... 514/220, 813

[56] References Cited

U.S. PATENT DOCUMENTS

| | | | |
|---|---|---|---|
| 5,229,382 | 7/1993 | Chakrabarti et al. | 514/220 |
| 5,321,012 | 6/1994 | Mayer et al. | 514/25 |

OTHER PUBLICATIONS

HCAPLUS Abstract 1995: 752833 (1995) Corbett et al.
HCAPLUS Abstract 1993: 662437 (1993) Ando et al.
J. Gerlach, et al., "Intolerance to neuroleptic drugs: the art of avoiding extrapyramidal syndromes", *European Psychiatry*, 10:1, pp. 27S–31S (1994).
J. P. McEvoy, et al., "Clozapine Decreases Drive to Smoke", *VIIth Biennial European Workshop on Schizophrenia, Les Diablerets, Switzerland*, Jan. 23–28, 46:5 (1994), Poster 28.
N. A. Moore, et al., "The Behavioral Pharmacology of Olanzapine, a Novel Atypical Antipsychotic Agent", *J. Pharm. Exp. Ther.*, 262:2, pp. 545–551 (1992).

*Primary Examiner*—Marianne M. Cintins
*Assistant Examiner*—M. Moezie
*Attorney, Agent, or Firm*—MaCharri Vorndran-Jones; David E. Boone

[57] ABSTRACT

The invention provides a method for treating a condition resulting from the cessation and withdrawal of nicotine comprising administering an effective amount of 2-methyl-4-(4-methyl-1-piperazinyl)-10H-thieno[2,3-b][1,5]-benzodiazepine.

17 Claims, No Drawings

METHOD FOR TREATING NICOTINE WITHDRAWAL

FIELD OF THE INVENTION

This invention provides a method for using 2-methyl-4-(4-methyl-1-piperazinyl)-10H-thieno[2,3-b][1,5]-benzodiazepine, for the treatment nicotine withdrawal and alleviation of the craving for a tobacco product.

BACKGROUND OF THE INVENTION

Over 25 years ago, the Surgeon General issued a report linking cigarette smoking to cancer, heart disease, respiratory disease and other conditions. Despite such information being available to the public, cigarette smoking remains a significant preventable cause of death in the United States and other developed countries.

Benowitz, N. Eng. J. Med. 319:20, 1318–1330 (Nov. 17, 1988) notes that many people who smoke cigarettes would like to quit but cannot because they are addicted to the psychoactive drug that is the dependence-producing constituent of tobacco, nicotine.

Benowitz notes that nicotine may also contribute to the diseases for which smoking is a risk factor, particularly heart disease. Nicotine is also present in other tobacco products that are smoked or chewed, which are also addictive and associated with heart, lung, and other serious disease states.

Pharmacologic therapies are known to help those addicted to nicotine. Receptor antagonists such as mecamylamine have been used to reduce the satisfaction obtained from tobacco use. Unfortunately, this therapy has the short term effect of increasing tobacco consumption to overcome the receptor antagonism as well as other undesirable side effects.

Non-receptor antagonists have also been used, such as clonidine to reduce the craving for tobacco and other tobacco related withdrawal symptoms. According to Benowitz, one recent study using clonidine treatment for six weeks was found to be more effective than placebo, but only for women.

Benowitz reports that the most effective treatment thus far has been nicotine substitution therapy, using nicotine gum, or other nicotine forms to slowly wean individuals from the addiction to nicotine and the tobacco products containing nicotine. Unfortunately, the nicotine substitution therapy involves the administration of the psychoactive constituent of tobacco which has been identified as a contributor to the diseases associated with smoking. Nicotine substitution must be tapered, frequently leading to nicotine withdrawal and subsequent relapse to smoking. There is a need for a therapy having a desirable side effect profile, to relieve nicotine withdrawal symptoms, including the long term cravings for nicotine.

It is known that the compound 2-methyl-4-(4-methyl-1-piperazinyl)-10H-thieno[2,3-b][1,5]benzodiazepine can provide antipsychotic activity and is less likely to induce extrapyramidal symptoms. Surprisingly, Applicant has discovered that 2-methyl-4-(4-methyl-1-piperazinyl)-10H-thieno[2,3-b][1,5]benzodiazepine can be useful for treating a condition which is a response produced by cessation and withdrawal from the use of nicotine. The compound 2-methyl-4-(4-methyl-1-piperazinyl)-10H-thieno[2,3-b][1,5]-benzodiazepine is known and described in U.S. Pat. No. 5,229,382, herein incorporated by reference in its entirety.

SUMMARY OF THE INVENTION

The presently claimed invention provides a method for treating a condition which is a response produced by cessation and withdrawal from the use of nicotine, comprising administering an effective amount of 2-methyl-4-(4-methyl-1-piperazinyl)-10H-thieno[2,3-b][1,5]benzodiazepine or a pharmaceutically acceptable salt thereof to a patient in need of such treatment.

DETAILED DESCRIPTION OF THE INVENTION

The 2-methyl-4-(4-methyl-1-piperazinyl)-10H-thieno[2,3-b][1,5]benzodiazepine compound is of the formula

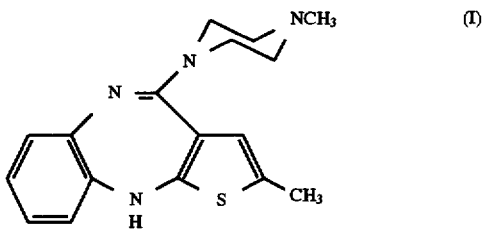

or an acid addition salt thereof. The free base of formula (I) is 2-methyl-4-(4-methyl-1-piperazinyl)-10H-thieno[2,3-b][1,5]benzodiazepine.

The substantially pure crystalline anhydrous Form I 2-methyl-4-(4-methyl-1-piperazinyl)-10H-thieno[2,3-b][1,5]-benzodiazepine (Form I) has a typical X-ray powder diffraction pattern substantially as follows, using a Sieman's D5000 diffractometer equipped with a copper radiation source, wherein d represents the interplanar spacing:

| d | $I/I_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

Form II 2-methyl-4-(4-methyl-1-piperazinyl)-10H-thieno[2,3-b][1,5]benzodiazepine (Form II) has a typical X-ray powder diffraction pattern substantially as follows, using a Sieman's D5000 diffractometer equipped with a copper radiation source, wherein d represents the interplanar spacing:

| d | I/I₁ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns set forth herein were obtained with a copper K of wavelength=1.541A. The interplanar spacings in the column marked "d" are in Angstroms. The typical relative intensities are in the column marked "I/I₁". The detector was a Kevex silicon lithium solid state detector.

As used herein "substantially pure" shall refer to anhydrous Form I associated with<5% Form II; and most preferably it shall refer to<2% Form II. It is further preferred that "substantially pure" shall refer to<0.5% non-Form I polymorph.

When the Form I polymorph is formulated as a pharmaceutical composition, "substantially pure" shall preferably refer to about<15% Form II polymorph; more preferably, the term shall refer to about<10% Form II polymorph when the Form I polymorph is formulated as a pharmaceutical, and it is especially preferred that the term shall refer to about<5% Form II polymorph when the substantially pure substance is formulated.

As used herein, the term "2-methyl-4-(4-methyl-1-piperazinyl)-10H-thieno[2,3-b][1,5]benzodiazepine" refers to a technical grade of 2-methyl-4-(4-methyl-1-piperazinyl)-10H-thieno[2,3-b][1,5]benzodiazepine when no specific solvate or polymorph is named. Typically, the technical grade 2-methyl-4-(4-methyl-1-piperazinyl)-10H-thieno[2,3-b][1,5]benzodiazepine contains less than about 5% undesired related substances and may be a mixed polymorph. Such technical grade 2-methyl-4-(4-methyl-1-piperazinyl)-10H-thieno[2,3-b][1,5]benzodiazepine may contain less than about 1% undesired related substances.

The term "crude" refers to a form of 2-methyl-4-(4-methyl-1-piperazinyl)-10H-thieno[2,3-b][1,5]benzodiazepine typically associated with undesired polymorph and/or greater than about 5% undesired related substances. Such crude grade 2-methyl-4-(4-methyl-1-piperazinyl)-10H-thieno[2,3-b][1,5]benzodiazepine may contain less than about 1% undesired related substances.

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

As used herein, the term "nicotine withdrawal" or "cessation and withdrawal from the use of nicotine" shall refer to a condition resulting from discontinued consumption of tobacco products and consequently, a result of discontinued consumption of nicotine. Such nicotine withdrawal conditions are characterized in the DSM-IV-R. *Diagnostic and Statistical Manual of Mental Disorders, Revised*, 3rd Ed. (1994). The DSM-IV-R was prepared by the Task Force on Nomenclature and Statistics of the American Psychiatric Association, and provides clear descriptions of diagnostic catagories. The skilled artisan will recognize that there are alternative nomenclatures, nosologies, and classification systems for pathologic psychological conditions and that these systems evolve with medical scientific progress.

Therefore, the term "cessation and withdrawal from the use of nicotine" shall include, but is not limited to, the following conditions characterized in the DSM-IV-R: Nicotine Withdrawal; Nicotine-Related Disorder Not otherwise Specified; Nicotine Dependence, with physiological dependence; Nicotine Dependence, without physiological dependence; Nicotine Dependence, Early Full Remission; Nicotine Dependence, Early Partial Remission; Nicotine Dependence, Sustained Full Remission; and Nicotine Dependence, Sustained Partial Remission; Nicotine Dependence, On Agonist Therapy.

The discontinued use of tobacco products, all of which contain nicotine, results in the onset of nicotine withdrawal syndrome. Individuals typically suffer the symptoms of nicotine withdrawal resulting from the discontinued use of tobacco in any form, including, but not limited to smoking of cigarette, cigar, or pipe tobacco, or the oral or intranasal ingestion of tobacco or chewing tobacco. Such oral or intranasal tobacco includes, but is not limited to snuff and chewing tobacco. The cessation of nicotine use or reduction in the amount of nicotine use, is often followed within 24 hours by dysphoric, depressed mood; insomnia; irritability, frustration or anger; anxiety; difficulty concentrating; restlessness; decreased heart rate; increased appetite or weight gain. These symptoms often cause clinically significant distress or impairment in social, occupational, or other important areas of functioning. The present invention is most preferably used to alleviate symptoms attributed to nicotine withdrawal when such symptoms are not due to a general medical condition and are not better accounted for by another medical disorder.

The method of the present invention is preferably administered in connection with and/or subsequent to an educational and/or behavioral modification program to ensure continued abstinence from tobacco products. The method of the present invention is also highly beneficial to such programs by alleviating the suffering experienced from the nicotine withdrawal over the course of such programs. Therefore, the programs can be more effective by focusing on educational and behavioral modification goals, further reducing the incidence of program non-completion.

Although the method of this invention is effective for any individual in need of treatment for the cessation and withdrawal of smoking, it may be particularly beneficial to use the method of this invention for an individual suffering from schizophrenia.

The results of pharmacological studies show that 2-methyl-4-(4-methyl-1-piperazinyl)-10H-thieno[2,3-b][1, 5]benzodiazepine has muscarinic cholinergic receptor activity. The compound is active at the dopamine D-1 and D-2 receptors as indicated by an IC50 of less than 1 uM in the $^3$H-SCH233390 (Billard, et al. Life Sciences 35:1885 (1984)) and the $^3$H spiperone (Seeman et al Nature 216:717 (1976)) binding assays respectively. Further, the anhydrous Form I compound is active at the 5-HT2 receptor and 5-HT1C receptor. The complex pharmacological profile of the compound provides a medicament which can be useful for the treatment of a condition resulting from cessation and withdrawal from the use of nicotine.

In vivo animal and clinical observations support that 2-methyl-4-(4-methyl-1-piperazinyl)-10H-thieno[2,3-b][1,5]benzodiazepine has a complex muscarinic receptor subtype profile. For example, rats exposed to an overdose of the compound surprisingly exhibited significant salivation. Further, clinical subjects experienced pupilary constriction rather than the expected pupilary dilation.

The usefulness of the compound for treating a condition resulting from cessation and withdrawal from the use of nicotine can be supported by the following study.

I. Auditory Startle Response.

Male Long Evans rats (Harlan Sprague Dawley) are individually housed in a controlled environment on a 12 hour light-dark cycle. The rats are given free access to food and water. All treatment groups contain from 8 to 10 rats.

The rats are anesthetized with halothane and Alzet osmotic minipumps (Alza Corporation, Palo Alto, Calif.) are implanted subcutaneously. Nicotine ditartrate is dissolved in physiological saline. Pumps are filled with nicotine ditartrate (6 mg/kg base/day) or the appropriate vehicle. Twelve days following implantation of pumps, rats are anesthetized with halothane and the pumps are removed.

The auditory Startle Response is observed.

The sensory motor reactions [auditory startle response (peak amplitude, $V_{max}$)] of individual rats are recorded using San Diego Instruments startle chambers (San Diego, Calif.). Startle sessions consist of a 5 minute adaptation period at background noise level of 70±2dBA immediately followed by 25 presentations of auditory stimuli (120±3 dBA noise, 50 ms duration) presented at 8 second intervals. Peak startle amplitudes are averaged for all 25 presentations of stimuli for each session. Auditory startle responding is evaluated daily at 24 hour intervals on days 1–4 following nicotine withdrawal.

The 2-methyl-4-(4-methyl-1-piperazinyl)-10H-thieno[2,3-b][1,5]benzodiazepine compound is administed at six doses about 60 minutes before startle testing each day.

The compound 2-methyl-4-(4-methyl-1-piperazinyl)-10H-thieno[2,3-b][1,5]benzodiazepine can be used for the methods of this invention, both in its free base and acid addition salt forms. The acid addition salts are preferably the pharmaceutically acceptable, non-toxic addition salts with suitable acids, such as those of inorganic acids, for example hydrochloric, hydrobromic, nitric, sulfuric or phosphoric acids, or of organic acids, such as organic carboxylic acids, for example glycollic, maleic, hydroxymaleic, fumaric, malic, tartaric, citric or lactic acid, or organic sulfonic acids for example methane sulfonic, ethane sulfonic, 2-hydroxyethane sulfonic, toluene-p-sulfonic or naphthalene-2-sulfonic acid.

The compound 2-methyl-4-(4-methyl-1-piperazinyl)-10H-thieno[2,3-b][1,5]benzodiazepine can be prepared using a process which comprises (a) reacting N-methylpiperazine with a compound of the formula

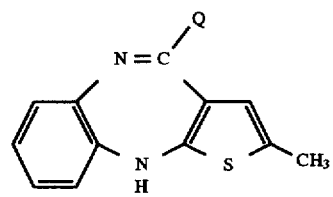
(II)

in which Q is a radical capable of being split off, or (b) ring-closing a compound of the formula

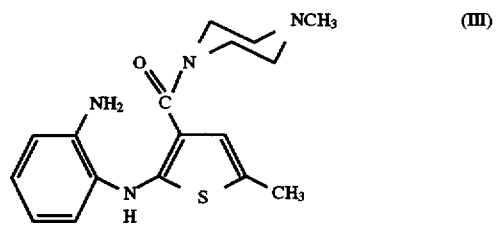
(III)

Appropriate reaction conditions and suitable values of Q can readily be chosen for these processes.

In reaction (a) the radical Q can, for example, be an amino group or a mono- or dialkyl-substituted amino group (each alkyl substituent suitably containing 1 to 4 carbon atoms), hydroxyl, thiol, or an alkoxy, alkylthio or alkylsulfonyl group suitably containing 1 to 4 carbon atoms, for example a methoxy or methylthio group, or a halogen atom, especially a chlorine atom. Preferably, Q is amino ($-NH_2$), hydroxyl or thiol, and amino is most preferred. The reaction is preferably carried out at a temperature of from 50° C. to 200° C.

When Q is amino, the intermediate of formula (II) may also exist in the imino form:

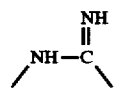

and when Q is hydroxyl or thiol, the intermediates of formula (II) may exist in their amide and thioamide forms:

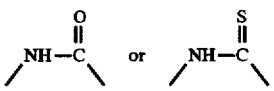

The amidine of formula (II) (Q is $-NH_2$), can be in salt form, for example a salt of a mineral acid such as the hydrochloride, and can be reacted with N-methylpiperazine in an organic solvent such as anisole, toluene, dimethylformamide or dimethylsulfoxide, preferably at a temperature range of 100 to 150° C.

The amidine is prepared by condensing a thiophene compound of formula

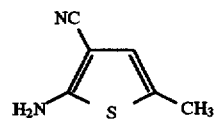

with an ortho-halonitrobenzene, in the presence of a base, for example sodium hydride, in a solvent such as tetrahydrofuran or n-butyl lithium in tetrahydrofuran, or potassium carbonate or lithium hydroxide in dimethylsulfoxide or aqueous sodium hydroxide in dimethylsulfoxide, or with a tetraalkyl-ammonium salt in a two-phase system, to form a nitronitrile of formula:

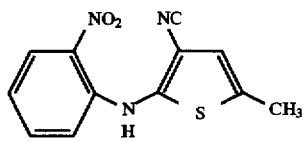 (IIa)

which can be simultaneously reduced and ring-closed to the amidine of formula (II) employing, for example, stannous chloride and hydrogen chloride in aqueous ethanol or, alternatively by reduction with hydrogen and palladium/ carbon or ammonium polysulfide followed by acid-catalyzed ring closure. The intermediate of formula (IIa) may be isolated using ammonium chloride ($NH_4Cl$) or ammonium acetate ($NH_4OAc$).

When Q is hydroxyl, reaction (a) is preferably carried out in the presence of titanium tetrachloride which has the ability to react with the N-methylpiperazine to form a metal amine complex. Other metal chlorides such as those of zirconium, hafnium or vanadium may also be employed. The reaction can be carried out in the presence of an acid binding agent such as a tertiary amine, for example, triethylamine.

Alternatively, the reaction can be carried out using excess of N-methylpiperazine to act as an acid-binding agent. A suitable organic solvent such as toluene or chlorobenzene can be used as a reaction medium, although the use of anisole is particularly desirable, at least as a co-solvent, in view of its ability to form a soluble complex with $TiCl_4$.

If desired, elevated temperatures, for example up to 200° C., can be used to hasten the reaction and a preferred temperature range for carrying out the reaction is from 80° C. to 120° C.

The intermediate amide of formula (II) (Q is —OH) can be prepared from the corresponding amidine (Q is —$NH_2$) by alkaline hydrolysis, or can be derived from compounds of formula

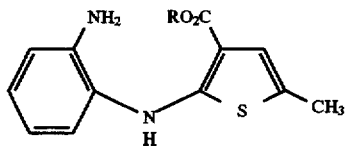 (IV)

in which R is an ester group, preferably $C_{1-4}$ alkyl, by ring closure employing, for example, sodium methylsulfinyl methanide in a suitable solvent such as dimethylsulfoxide. Alternatively, the amide can be prepared by ring closure of an amino-acid, employing for example dicyclohexylcarbodiimide (DCC) in a suitable solvent such as tetrahydrofuran. The amino-acid can be obtained for example from the above esters by basic hydrolysis using for example sodium hydroxide in ethanol.

Thioamides of formula (II) (Q is —SH), iminothioethers, iminoethers or iminohalides, or other derivatives containing active Q radicals as specified above, tend to be more reactive towards N-methylpiperazine and can usually be reacted without the necessity for the presence of $TiCl_4$, but otherwise employing the same conditions of temperature and solvent.

The thioamide of formula (II) (Q is —SH) can be prepared by treating a solution of the corresponding amide in an anhydrous basic solvent, such as pyridine, with phosphorous pentasulfide. Similarly, the amide can be converted to the iminothioether, iminoether or iminohalide, or other derivatives containing active Q radicals, by treatment with conventional reagents such as for example in the case of the iminochloride, phosphorous pentachloride.

The intermediate compounds of formula (II) in which Q is a radical capable of being split off, particularly those in which Q is —$NH_2$, —OH or —SH and when Q is —$NH_2$ salts thereof, are novel compounds, and form a further aspect of the present invention.

With regard to reaction (b) above, the compound of formula (III) may be ring-closed by employing, for example, titanium tetrachloride as catalyst and anisole as solvent, and the reaction is preferably carried out at a temperature of 100° C. to 250° C., for example from 150° C. to 200° C.

The intermediate compound of formula (III) is preferably prepared in situ without isolation by reacting a compound of formula

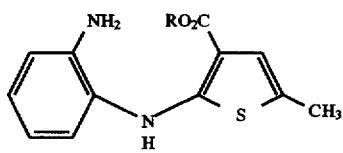 (IV)

in which R is an ester group, preferably $C_{1-4}$ alkyl, with N-methylpiperazine, by heating to a temperature of between 30° C. and 120° C., for example about 100° C., in a suitable solvent such as for example anisole, and employing $TiCl_4$ as catalyst.

The compound of formula (IV) can be prepared from the corresponding nitro compound of formula

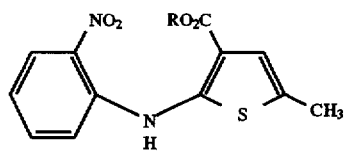 (V)

Such compounds of formula (V) in which R is an ester group, such as for example $C_{1-4}$ alkyl, are novel and form a further aspect of the invention.

If convenient this nitro compound can be converted to the amine of formula (IV) without isolation, before reaction with N-methylpiperazine. Intermediate compounds of formula (V) can be made by condensation of a thiophene of formula

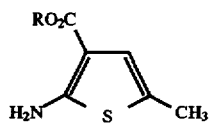 (VI)

with an ortho-halonitrobenzene, preferably ortho fluoro- or chloro- nitrobenzene, in the presence of a base, for example, (a) sodium hydride in a solvent such as for example tetrahydrofuran and at a temperature of from −20° C. to 30° C., or (b) anhydrous potassium carbonate or lithium hydroxide in a solvent such as dimethylsulfoxide at a temperature of from 90° C. to 120° C. The compound of formula (V) is converted to that of formula (IV) by reduction, for example catalytically, employing hydrogen and palladium/carbon, or chemically, employing stannous chloride and hydrogen chloride in aqueous ethanol, or ammonium polysulfide, or zinc in aqueous ammonium chloride.

It will be appreciated that the compound of formula (I) may be isolated per se or may be converted to an acid addition salt using conventional methods.

The compound has an $IC_{50}$ of less than 1 mM in the $^3$H-QNB binding assay described by Yamamura, HI and Snyder, SH in Proc.Nat.Acad.Sci. USA 71 1725 (1974) indicating that it has muscarinic-cholinergic activity.

The 2-methyl-4-(4-methyl-1-piperazinyl)-10H-thieno-[2,3-b][1,5]benzodiazepine compound is effective over a wide dosage range, the actual dose administered being dependent on the condition being treated. For example, in the treatment of adult humans, dosages of from about 0.25 to 50 mg, preferably from 1 to 30 mg, and most preferably 1 to 20 mg per day may be used. A once a day dosage is normally sufficient although divided doses may be administered. For treatment of a condition resulting from cessation and withdrawal from the use of nicotine, a dose range of from 1 to 30 mg, preferably 1 to 20 mg per day is suitable. Radiolabelled 2-methyl-4-(4-methyl-1-piperazinyl)-10H-thieno-[2,3-b][1,5]benzodiazepine, can be detected in the saliva and thus the compound can potentially be monitored in patients to assess compliance.

A preferred formulation of the invention is a solid oral formulation comprising from about 1 to about 20 mg or 1 to 10 mg of active anhydrous Form I 2-methyl-4-(4-methyl-1-piperazinyl)-10H-thieno[2,3-b][1,5]benzodiazepine as an effective amount of the active ingredient.

Most preferably, the solid oral formulation is contained in packaging materials which protect the formulation from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

The 2-methyl-4-(4-methyl-1-piperazinyl)-10H-thieno-[2,3-b][1,5]benzodiazepine compound will normally be administered orally or by injection and, for this purpose, it is usually employed in the form of a pharmaceutical composition.

Accordingly, pharmaceutical compositions comprising 2-methyl-4-(4-methyl-1-piperazinyl)-10H-thieno[2,3-b][1,5]benzodiazepine, as active ingredient associated with a pharmaceutically acceptable carrier may be prepared. In making the compositions of the invention conventional techniques for the preparation of pharmaceutical compositions may be used. For example, the active ingredient will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. The active ingredient can be adsorbed on a granular solid container for example in a sachet. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxy-benzoate, talc, magnesium stearate or mineral oil. The compositions of the invention may, if desired, be formulated so as to provide quick, sustained or delayed release of the active ingredient after administration to the patient. For example, one such preferred quick release formulation is described in U.S. Pat. Nos. 5,079,018, 5,039,540, 4,305,502, 4,758,598, and 4,371,516, hereby incorporated by reference. Such formulation most preferably comprises 2-methyl-4-(4-methyl-1-piperazinyl)-10H-thieno[2,3-b][1,5]benzodiazepine, water, hydrolyzed gelatin, and mannitol.

Depending on the method of administration, the compositions for the treatment of central nervous system conditions may be formulated as tablets, capsules, injection solutions for parenteral use, gel or suspension for transdermal delivery, suspensions or elixirs for oral use or suppositories. Preferably the compositions are formulated in a unit dosage form, each dosage containing from 0.25 to 100 mg, more usually 1 to 30 mg, of the active ingredient. When a sustained release formulation is desired, the unit dosage form may contain from 0.25 to 200 mg of the active ingredient. A preferred formulation of the invention is a capsule or tablet comprising 0.25 to 75 mg or 1 to 30 mg of active ingredient together with a pharmaceutically acceptable carrier therefor. A further preferred formulation is an injection which in unit dosage form comprises 0.25 to 30 mg or 1 to 30 mg of active ingredient together with a pharmaceutically acceptable diluent therefor.

The materials for the present invention can be purchased or prepared by a variety of procedures well known to those of ordinary skill in the art. The 2-methyl-4-(4-methyl-1-piperazinyl)-10H-thieno[2,3-b][1,5]benzodiazepine compound can be prepared as described by Chakrabarti in U.S. Pat. No. 5,229,382 ('382), herein incorporated by reference in its entirety. It is most desirable to prepare a rapidly dissolving formulation comprising substantially pure crystalline Form I 2-methyl-4-(4-methyl-1-piperazinyl)-10H-thieno[2,3-b][1,5]benzodiazepine. Such substantially pure crystalline Form I 2-methyl-4-(4-methyl-1-piperazinyl)-10H-thieno[2,3-b][1,5]benzodiazepine may be prepared using the techniques described herein by the Preparation section herein infra.

As used herein mixing steps may be accomplished using common agitation methods such as stirring, shaking, and the like. As used herein the phrase "producing crystalline product from the mixture" shall refer to crystallization from the stated mixture of compound and solvent. Further, the artisan recognizes that crystallization processes may include seeding, chilling, scratching the glass of the reaction vessel, and other such common techniques.

Compound characterization methods include, for example, x-ray powder pattern analysis, thermogravimetric analysis (TGA), differential scanning calorimetery (DSC), titrametric analysis for water, and $H^1$-NMR analysis for solvent content.

The following examples are provided for purposes of illustration and are not to be construed as limiting the scope of the claimed invention.

PREPARATION 1

Crystalline Form II 2-methyl-4-(4-methyl-1-piperazinyl)-10H-thieno[2,3-b][1,5]benzodiazepine A 10 gram sample of crude 2-methyl-4-(4-methyl-1-piperazinyl)-10H-thieno[2,3-b][1,5]benzodiazepine was suspended in methylene chloride (100)gm and stirred at ambient temperature (20°–25° C.) for a period of 1 hour. The slurry was vacuum filtered and the filtrate was recovered. The stirred filtrate was chilled to 0°–5° C. in an ice bath and the solvent was slowly evaporated under a stream of nitrogen to a thick paste. Approximately ¾ of the solvent was removed by evaporation. A quantity of prechilled methylene chloride (30 gm, 0°–5° C.) was mixed into the thick paste. The resulting slurry was vacuum filtered and allowed to air dry on the filter. The isolated solid was further dried in a vacuum oven at 50° C. for a period of 30 minutes. Isolated: 4.8 gm. X-ray powder characterization: Form II+$CH_2Cl_2$ Solvate.

The isolated solid was redried in a vacuum oven at 50° C. under a stream of nitrogen for a period of 30 hours Isolated: 4.5 gm X-ray powder characterization: Form II. (described supra.)

PREPARATION 2

Form I 2-methyl-4-(4-methyl-1-piperazinyl)-10H-thieno[2,3-b][1,5]benzodiazepine

A sample of ethyl acetate which was saturated with technical grade 2-methyl-4-(4-methyl-1-piperazinyl)-10H-thieno[2,3-b][1,5]benzodiazepine was contacted with Form II 2-methyl-4-(4-methyl-1-piperazinyl)-10H-thieno[2,3-b][1,5]benzodiazepine (0.3 g), a seed of anhydrous Form I 2methyl-4-(4-methyl-1-piperazinyl)-10H-thieno[2,3-b][1,5]benzodiazepine and stirred at about 25° C. for about 5 hours. The reaction product was isolated by vacuum filtration and dried under ambient conditions. Yield: 0.25 g. X-ray powder analysis indicated that the product was anhydrous Form I 2-methyl-4-(4-methyl-1-piperazinyl)-10H-thieno[2,3-b][1,5]benzodiazepine.

PREPARATION 3

Technical Grade 2-methyl-4-(4-methyl-1-piperazinyl)-10H-thieno[2,3-b][1,5]benzodiazepine

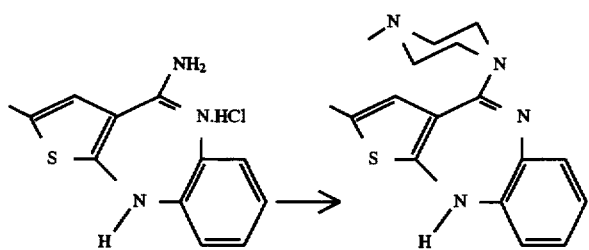

Intermediate 1

In a suitable three neck flask the following was added:
Dimethylsulfoxide (analytical): 6 volumes
Intermediate 1: 75 g
N-Methylpiperazine (reagent): 6 equivalents Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained throughout the duration of the reaction. The reactions were followed by HPLC until ≦5% of the intermediate 1 was left unreacted. After the reaction was complete, the mixture was allowed to cool slowly to 20° C. (about 2 hours). Each reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical 2-methyl-4-(4-methyl-1-piperazinyl)-10H-thieno[2,3-b][1,5]benzodiazepine.

Yield: 76.7%; Potency: 98.1%

The procedure of Preparation 3 was repeated substantially as described above and provided a yield of 81% with a potency of 101.1%.

PREPARATION 4

Technical Grade 2-methyl-4-(4-methyl-1-piperazinyl)-10H-thieno[2,3-b][1,5]benzodiazepine Intermediate 1 (supra) was suspended in DMSO (3.2 vol.) and toluene (4.5 vol.). A portion (≈0.65 vol.) of the solvent was removed by distillation at 120°–125° C. The mixture was cooled to 110° C., N-methylpiperazine(NMP, 4.2 equiv.) was added and the mixture heated back to reflux (120°–125° C.). Another portion (≈1 vol.) of the solvent was removed by distillation to dry the reaction mixture. A vigorous reflux was desired to drive the reaction to completion (about 7 hrs.) by removing ammonia from the reaction. The product was isolated by the slow addition of water (12.75 vol.) to the cooled (10° C.) reaction solution. The product was collected by filtration and washed with chilled water (2 vol.). The crude 2-methyl-4-(4-methyl-1-piperazinyl)-10H-thieno[2,3-b][1,5]benzodiazepine was dried in vacuo at 60° C. The product was recrystallized from hot toluene (5 vol.) to give a technical grade 2-methyl-4-(4-methyl-1-piperazinyl)-10H-thieno[2,3-b][1,5]benzodiazepine. After drying in vacuo at 50° C., the technical grade 2-methyl-4-(4-methyl-1-piperazinyl)-10H-thieno[2,3-b][1,5]benzodiazepine was recrystallized again from ethyl acetate (10 vol.)/toluene (0.62 vol.)/methanol (3.1 vol.)to give 2-methyl-4-(4-methyl-1-piperazinyl)-10H-thieno[2,3-b][1,5]benzodiazepine as a methanol solvate. The methanol solvate upon drying at>50° C. was converted to an anhydrous technical grade 2-methyl-4-(4-methyl-1-piperazinyl)-10H-thieno[2,3-b][1,5]benzodiazepine.

PREPARATION 5

Form I from acetone

A 3.0 g sample of technical grade 2-methyl-4-(4-methyl-1-piperazinyl)-10H-thieno[2,3-b][1,5]benzodiazepine was suspended in acetone (30 g). The mixture was stirred and heated to about 60° C. The mixture was maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5]benzodiazepine using x-ray powder analysis. Yield: 0.8 g.

PREPARATION 6

Form I Using tetrahydrofuran

An 8.0 g sample of technical grade 2-methyl-4-(4-methyl-1-piperazinyl)-10H-thieno[2,3-b][1,5]benzodiazepine was suspended in tetrahydrofuran (25 g). The mixture was stirred and heated to about 60° C. The mixture was maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5]benzodiazepine using x-ray powder analysis. Yield: 1.3 g.

PREPARATION 7

Form I Using ethyl acetate

A 270 g sample of technical grade 2-methyl-4-(4-methyl-1-piperazinyl)-10H-thieno[2,3-b][1,5]benzodiazepine was suspended in ethyl acetate (2.7 L). The mixture was heated to about 76° C. and maintained at about 76° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5]benzodiazepine using x-ray powder analysis. Yield: 197 g.

PREPARATION 8

Form I from t-butanol

A 1.0 g sample of technical grade 2-methyl-4-(4-methyl-1-piperazinyl)-10H-thieno[2,3-b][1,5]benzodiazepine was suspended in tert-butanol (30 g). The stirred mixture was heated to about 60° C. and maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5]benzodiazepine using x-ray powder analysis. Yield: 0.3 g.

PREPARATION 9

Form I from Slurry Conversion of Form II in Toluene

A 0.5 g sample of technical grade 2-methyl-4-(4-methyl-1-piperazinyl)-10H-thieno[2,3-b][1,5]benzodiazepine and a 0.5 g sample of Form II 2-methyl-4-(4-methyl-1-piperazinyl)-10H-thieno[2,3-b][1,5]benzodiazepine were suspended in toluene (5 ml), presaturated with 2-methyl-4-(4-methyl-1-piperazinyl)-10H-thieno[2,3-b][1,5]benzodiazepine. The mixture was stirred in a sealed vial at about ambient temperature for about 22 hours. The resulting product was isolated using vacuum filtration and dried under vacuum at about 45° C. The product was identified as Form I 2-methyl-4-(4-methyl-1-piperazinyl)-10H-thieno[2,3-b][1,5]benzodiazepine using x-ray powder analysis.

EXAMPLE 1

A portion of the hydroxypropyl cellulose was dissolved in purified water to form a solution for granulation. The remaining hydroxypropyl cellulose (total of 4.0% w/w final tablet weight), which was an extra fine grade, was combined with the 2-methyl-4-(4-methyl-1-piperazinyl)-10H-thieno[2,3-b][1,5]benzodiazepine (1.18% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The running powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating

Hydroxypropyl methylcellulose (10% w/w) was mixed with purified water to form a solution. Core tablets were divided into approximately equal sections and spray coated with the hydroxypropyl methylcellulose solution. The operation was performed in a perforated coating pan.

Coating of Core Tablets

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

EXAMPLE 2

The process substantially as described above in Example 1 was repeated using the following ingredients to provide pharmaceutically elegant tablet formulations containing 1, 2.5, 5, 7.5, and 10 mg 2-methyl-4-(4-methyl-1-piperazinyl)-10H-thieno[2,3-b][1,5]benzodiazepine, respectively, per tablet:

1 mg 2-methyl-4-(4-methyl-1-piperazinyl)-10H-thieno[2,3-b][1,5]benzodiazepine per tablet

| Names of Ingredients | Quantity (mg/tablet) |
|---|---|
| Active Ingredient | |
| 2-methyl-4-(4-methyl-1-piperazinyl)-10H-thieno[2,3-b][1,5]benzodiazepine | 1.0 |
| Other Ingredients | |
| Lactose | 67.43 |
| Hydroxypropyl Cellulose | 3.40 |
| Crospovidone | 4.25 |
| Microcrystalline Cellulose | 8.50 |
| Magnesium Stearate | 0.42 |
| Subcoating | |
| Hydroxypropyl Methylcellulose Coating | 1.70 |
| Color Mixture White Polishing | 3.47 |
| Carnauba Wax Imprinting | trace |
| Edible Blue Ink | trace |

2-methyl-4-(4-methyl-1-piperazinyl)-10H-thieno[2,3-b][1,5]benzodiazepine 2.5 mg Tablets

| Names of Ingredients | Quantity (mg/tablet) |
|---|---|
| Active Ingredient | |
| 2-methyl-4-(4-methyl-1-piperazinyl)-10H-thieno[2,3-b][1,5]benzodiazepine | 2.5 |
| Other Ingredients | |
| Lactose | 102.15 |
| Hydroxypropyl Cellulose | 5.20 |
| Crospovidone | 6.50 |
| Microcrystalline Cellulose | 13.00 |
| Magnesium Stearate | 0.65 |
| Subcoating | |
| Hydroxypropyl Methylcellulose Coating | 2.60 |
| Color Mixture White Polishing | 5.30 |
| Carnauba Wax Imprinting | trace |
| Edible Blue Ink | trace |

2-methyl-4-(4-methyl-1-piperazinyl)-10H-thieno[2,3-b][1,5]benzodiazepine 5.0 mg Tablets

| Names of Ingredients | Quantity (mg/tablet) |
|---|---|
| Active Ingredient | |
| 2-methyl-4-(4-methyl-1-piperazinyl)-10H-thieno[2,3-b][1,5]benzodiazepine | 5.00 |
| Other Ingredients | |
| Lactose | 156.00 |
| Hydroxypropyl Cellulose | 8.00 |
| Crospovidone | 10.00 |
| Microcrystalline Cellulose | 20.00 |
| Magnesium Stearate | 1.00 |
| Subcoating | |
| Hydroxypropyl Methylcellulose Coating | 4.00 |
| Color Mixture White Polishing | 8.16 |
| Carnauba Wax Imprinting | trace |
| Edible Blue Ink | trace |

2-methyl-4-(4-methyl-1-piperazinyl)-10H-thieno[2,3-b][1,5]benzodiazepine 7.5 mg Tablets

| Names of Ingredients | Quantity (mg/tablet) |
|---|---|
| Active Ingredient | |
| 2-methyl-4-(4-methyl-1-piperazinyl)-10H-thieno[2,3-b][1,5]benzodiazepine | 7.50 |
| Other Ingredients | |
| Lactose | 234.00 |
| Hydroxypropyl Cellulose | 12.00 |
| Crospovidone | 15.00 |
| Microcrystalline Cellulose | 30.00 |
| Magnesium Stearate | 1.50 |
| Subcoating | |
| Hydroxypropyl Methylcellulose Coating | 6.00 |
| Color Mixture White Polishing | 12.24 |
| Carnauba Wax Imprinting | trace |
| Edible Blue Ink | trace |

2-methyl-4-(4-methyl-1-piperazinyl)-10H-thieno[2,3-b][1,5]benzodiazepine 10.0 mg Tablets

| Names of Ingredients | Quantity (mg/tablet) |
|---|---|
| Active Ingredient | |
| 2-methyl-4-(4-methyl-1-piperazinyl)-10H-thieno[2,3-b][1,5]benzodiazepine | 10.00 |
| Other Ingredients | |
| Lactose | 312.00 |
| Hydroxypropyl Cellulose | 16.00 |
| Crospovidone | 20.00 |
| Microcrystalline Cellulose | 40.00 |
| Magnesium Stearate | 2.00 |
| Subcoating | |
| Hydroxypropyl Methylcellulose Coating | 8.00 |
| Color Mixture White Polishing | 16.32 |
| Carnauba Wax Imprinting | trace |
| Edible Blue Ink | trace |

EXAMPLE 4

Pulvule Formulation

A pulvule formulation is prepared by blending the active with silicone starch, and filling it into hard gelatin capsules.

| | Per 300 mg capsule |
|---|---|
| Compound of the invention | 30.0 mg |
| Silicone | 2.9 mg |
| Starch flowable | 267.1 mg |

EXAMPLE 5

Tablet Formulation

A tablet formulation is made by granulating the active with appropriate diluent, lubricant, disintegrant and binder and compressing

| | |
|---|---|
| Compound of the invention | 10.0 mg |
| Magnesium stearate | 0.9 mg |
| Microcrystalline cellulose | 75.0 mg |
| Povidone | 15.0 mg |
| Starch, directly compressible | 204.1 mg |

EXAMPLE 6

Aqueous Injection Formulation

An aqueous injection of active is prepared as a freeze-dried plug, for reconstitution in a suitable, sterile diluent before use (to a total volume of 10 ml).

Compound of the invention is contacted with Mannitol N Hydrochloric acid and/or N sodium hydroxide to adjust pH to 5–5.5.

| | |
|---|---|
| Compound of the invention | 20.0 mg |
| Mannitol | 20.0 mg |
| N Hydrochloric acid and/or N sodium hydroxide to adjust pH to 5–5.5 | |

EXAMPLE 7

Controlled Release IM Formulation

A controlled release injection for intramuscular injection is formed from a sterile suspension of micronised active in an oleaginous vehicle.

| | |
|---|---|
| Compound of the invention | 50.0 mg |
| Aluminium stearate | 0.04 mg |
| Sesame oil | 2 ml |

EXAMPLE 8

Capsule Formulation

A formulation is prepared by blending the active with silicone starch and starch, and filling it into hard gelatine capsules.

| | Per 300 mg capsule |
|---|---|
| Compound of the invention | 2.5 mg |
| Starch flowable with 0.96% silicone 220 | 222.5 mg |
| Starch flowable | 75.0 mg |

EXAMPLE 9

2-methyl-4-(4-methyl-1-piperazinyl)-10H-thieno[2,3-b][1,5]benzodiazepine Granules The granules were produced by blending the mannitol and Hydroxymethyl propyl cellulose in a high shear mixer; granulating with the aqueous suspension of 2-methyl-4-(4-methyl-1-piperazinyl)-10H-thieno[2,3-b][1,5]benzodiazepine and polysorbate 20; wet sized and subsequently dried in a fluid bed dryer. These are dry sized and reblended prior to packaging.

| INGREDIENT | MG/SACHET |
|---|---|
| 1a. 250 mg total weight Sachets | |
| Active | |
| 2-methyl-4-(4-methyl-1-piperazinyl)-10H-thieno[2,3-b][1,5]benzodiazepine | 2.50 |
| Other Ingredients | |
| Mannitol | 234.97 |
| Hydroxypropyl methyl cellulose 3 cps | 12.50 |
| Polysorbate 20 | 0.028 |

—continued

| INGREDIENT | MG/SACHET |
|---|---|
| 1b. 750 mg total weight Sachets | |
| Active | |
| 2-methyl-4-(4-methyl-1-piperazinyl)-10H-thieno[2,3-b][1,5]benzodiazepine | 7.50 |
| Other Ingredients | |
| Mannitol | 704.93 |
| Hydroxypropyl methyl cellulose 3 cps | 37.49 |
| Polysorbate 20 | 0.08 |
| 1c. 1000 mg total weight Sachets | |
| Active | |
| 2-methyl-4-(4-methyl-1-piperazinyl)-10H-thieno[2,3-b][1,5]benzodiazepine | 10.0 |
| Other Ingredients | |
| Mannitol | 939.90 |
| Hydroxypropyl methyl cellulose 3 cps | 49.99 |
| Polysorbate 20 | 0.11 |

Such granules are most preferably contacted with an acidic medium if a suspension or solution is desired.

I claim:

1. A method for treating a mammal suffering withdrawal from or dependence on nicotine, comprising administering an effective amount of 2-methyl-4-(4-methyl-1-piperazinyl)-10H-thieno[2,3-b][1,5]benzodiazepine, or a pharmaceutically acceptable salt thereof, to the mammal.

2. A method of claim 1 wherein the 2-methyl-4-(4-methyl-1-piperazinyl)-10H-thieno[2,3-b][1,5]benzodiazepine is substantially pure Form I having a typical X-ray powder diffraction pattern substantially as follows, using a Sieman's DS5000 diffractometer wherein d represents the interplanar spacing in Angstroms:

d
10.2689
8.577
7.4721
7.125
6.1459
6.071
5.4849
5.2181
5.1251
4.9874
4.7665
4.7158
4.4787
4.3307
4.2294
4.141
3.9873
3.7206
3.5645
3.5366
3.3828

3.2516
3.134
3.0848
3.0638
3.0111
2.8739
2.8102
2.7217
2.6432
2.6007.

3. A method of claim 1 wherein the nicotine withdrawal or dependence is from the smoking of tobacco.

4. A method of claim 3 wherein the nicotine withdrawal or dependence is from the smoking of cigarettes.

5. A method of claim 1 wherein the nicotine dependence is selected from the group consisting of Nicotine Dependence, with physiological dependence; Nicotine Dependence, without physiological dependence; Nicotine Dependence, Early Full Remission; Nicotine Dependence, Early Partial Remission; Nicotine Dependence, Sustained Full Remission; Nicotine Dependence, Sustained Partial Remission; and Nicotine Dependence, On Agonist Therapy.

6. A method of claim 1 wherein the mammal is suffering from Nicotine Withdrawal.

7. A method of claim 1 wherein the nicotine withdrawal or dependence is from the oral ingestion of tobacco.

8. A method of claim 2 wherein the nicotine dependence is selected from the group consisting of Nicotine Dependence, with physiological dependence; Nicotine Dependence, without physiological dependence; Nicotine Dependence, Early Full Remission; Nicotine Dependence, Early Partial Remission; Nicotine Dependence, Sustained Full Remission; Nicotine Dependence, Sustained Partial Remission; and Nicotine Dependence, On Agonist Therapy.

9. A method of claim 2 wherein the mammal is suffering from Nicotine Withdrawal.

10. A method of claim 1 wherein the effective amount is from about 1 mg to about 20 mg per day.

11. A method of claim 1 wherein the mammal is a human.

12. A method of claim 3 wherein the mammal is a human.

13. A method of claim 4 wherein the mammal is a human.

14. A method of claim 2 wherein the mammal is a human.

15. A method of claim 8 wherein the mammal is a human.

16. A method of claim 9 wherein the mammal is a human.

17. A method of claim 10 wherein the mammal is a human.

* * * * *